United States Patent [19]

Lin

[11] Patent Number: 6,013,847

[45] Date of Patent: Jan. 11, 2000

[54] HYDROGENATION OF BENZENE IN THE PRESENCE OF WATER

[75] Inventor: Fan-Nan Lin, Bartlesville, Okla.

[73] Assignee: Phillips Petroleum Company, Bartlesville, Okla.

[21] Appl. No.: 09/223,932

[22] Filed: Dec. 31, 1998

[51] Int. Cl.[7] .................................................. C07C 5/10
[52] U.S. Cl. ...................... 585/269; 585/266; 585/272; 585/277; 208/144
[58] Field of Search ........................... 208/144; 585/266, 585/269, 272, 277

[56] References Cited

U.S. PATENT DOCUMENTS

| | | | |
|---|---|---|---|
| 3,639,227 | 2/1972 | Jacobson et al. | 208/143 |
| 3,816,299 | 6/1974 | Mears | 208/143 |
| 4,212,990 | 7/1980 | Yasuhara et al. | 560/241 |
| 4,508,918 | 4/1985 | Yasuhara et al. | 560/241 |
| 5,457,252 | 10/1995 | Gill et al. | 585/269 |
| 5,777,186 | 7/1998 | Shimizu | 585/269 |
| 5,789,637 | 8/1998 | Mignard et al. | 585/269 |

*Primary Examiner*—Walter D. Griffin
*Assistant Examiner*—Nadine Preisch

[57] ABSTRACT

Benzene is hydrogenated using a platinum containing catalyst in the presence of water and an organic chloride.

6 Claims, No Drawings

HYDROGENATION OF BENZENE IN THE PRESENCE OF WATER

BACKGROUND OF THE INVENTION

The present invention relates to a process for benzene hydrogenation in the presence of an impurity in the benzene-containing feedstock.

The use of supported platinum catalysts, such as platinum on zeolite, as catalyst for the hydrogenation of benzene is well known. It is also known that water acts as a deactivating agent, catalyst poison, for platinum catalysts. Pretreatment of the feedstock to hydrogenation processes to remove water is common practice. Water, however, often remains in the feedstock after drying treatments in a quantity in the part per million range which, depending on the reaction process, is often adequate to have a noticeable deactivating effect.

SUMMARY OF THE INVENTION

The object of this invention is to hydrogenate a feedstock containing benzene and a small quantity of water in the presence of a platinum containing catalyst also in the presence of a compound that acts to alleviate, or essentially eliminate, the catalyst deactivation.

According to the invention, in a process for hydrogenating a feedstock containing benzene in a reaction zone containing an amount of water sufficient to deactivate the hydrogenation catalyst wherein the reaction zone contains (1) up to about 20% by weight benzene, (2) hydrogen gas, and (3) water in an amount up to about 30 parts per million parts by weight of a total feedstream that also contains the benzene and wherein the feedstream is contacted in the reaction zone with a hydrogenation catalyst comprising platinum under conditions effective to hydrogenate benzene, wherein deactivation of the catalyst occurs the improvement comprises at least alleviating the deactivation of the catalyst caused by the presence of water by having at least one organic chlorine compound present in the reaction zone.

DETAILED DESCRIPTION OF THE INVENTION

Any effective catalyst which contains platinum can be employed in the process of this invention. Preferably the platinum is supported, more preferably it is supported on a zeolite. Any effective zeolite can be employed as the support material. Non-limiting examples include, but are not limited to, zeolite X, zeolite Y, zeolite L, zeolite Beta, zeolite ZSM-5, zeolite ZSM-11, zeolite ZSM-12, zeolite ZSM-22, zeolite ZSM-23, zeolite ZSM-35, zeolite ZSM-48, erionite, mordenite, and the like and mixtures of one or more thereof. Some of the Pt/zeolite catalysts are commercially available, e.g. from UOP, Des Plains, Ill. Generally the platinum content in the catalyst ranges from about 0.05 to 2.0 weight% platinum and the surface area of the catalyst is about 100–800 $m^2g$, measured by the BET method. The catalyst can be fresh (unused) or it can be a used catalyst that has been regenerated.

Any reaction conditions suitable for the hydrogenation of benzene can be employed in practicing this invention. Generally the feed hydrocarbons and hydrogen gas are premixed and are contacted with the catalyst, which is generally present in a fixed bed, at a reaction temperature of at least 100° F., preferably in a range of about 100° F. to about 300° F., more preferably in a range of about 150° F. to about 250° F. Generally, the molar ratio of hydrogen gas to total feedstream is within the range of about 0.01:1 to about 10:1, preferably about 0.1:1 to about 1:1. The liquid hourly space velocity (cc of liquid feed per cc of catalyst per hour) of the hydrocarbon feedstream is, generally, about 0.1 to about 10 and the reaction pressure is within the range of about 200 psig to about 700 psig, preferably about 400 psig to about 500 psig. The gas hourly space velocity of the hydrogen stream is, generally, 10–2000 (preferably 50–200) cc $H_2$ per cc catalyst per hour to maintain the $H_2$:total feedstream ratio recited above.

For the purposes of this invention, the amount of benzene present in the total feedstock is limited to about 20 weight %, preferably from about 10 weight % to about 20 weight % so that the effluent from the hydrogenation can be practically free of benzene. The effluent from the hydrogenation should contain no more than 100 ppm benzene.

Also for the purposes of this invention, the amount of water present in the feedstock is limited to about 30 ppm or less. As a practical matter, the presence of water at 5 ppm or less may not seriously effect the reaction so the range could be set at about 5 to about 30 ppm.

HCl can be used as the chlorine containing additive, but organic chlorides are presently preferred. Compounds that are effective to promote the activity of the catalyst and thereby alleviate the deleterious effects of the presence of water in the process of this invention can be chosen from, but are not limited to the following organic chlorides: chloroalkanes, chlorocycloalkanes, and chloroalkenes and preferably including monochloromethane, dichloromethane, trichloromethane, tetrachloromethane, monochloroethane, dichloroethanes, trichloroethanes, tetrachloroethanes, pentachloroethane, hexachloroethane, monchloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentanes, dichloropentanes, trichloropentanes, tetrachloropentanes, monochlorocyclopentane, chlorohexanes, dichlorocyclopentanes, trichlorocyclopentanes, monochloroethylene, 1,1-dichloroethylene, 1,2-dichloroethylene, trichloroethylene, tetrachloroethylene (perchloroethylene, PEC), chloropropylenes, chloro-n-butenes, chloroisobutenes, chloropentenes and mixtures of one or more thereof. Of these, tetrachloroethylene (perchloroethylene) is most preferred because of its availability.

The amount of organic chloride necessary to counter the deactivating effect to a hydrogenation reaction catalyzed using platinum of the presence of water in the feedstock and to promote the hydrogenation of benzene is in the range of about 25 ppm to about 150 ppm, preferably from about 50 ppm to about 100 ppm, in the total feedstock of the hydrogenation process. The organic chloride can be injected into either the hydrocarbon stream, the hydrogen stream or into a combined feed stream of hydrocarbons and hydrogen if these streams are combined upstream of the reaction zone.

The following example is presented to further illustrate the invention and is not to be considered as unduly limiting the invention.

EXAMPLE I

A stainless steel reactor (having an inner diameter of 0.75 inch and a height of about 31 inches) was charged between layers of inert alumina particles with 20 cc of H-8, a commercial catalyst containing platinum (marketed by UOP, Des Plaines, Ill.). The reactor contents were heated to about 100° F. and a liquid feedstock containing 13.5 weight % of benzene and 9 ppm of water was introduced into the reactor at a liquid hourly space velocity of 2 cc/cc/hr together with a hydrogen gas flow of 0.5 scf/hr and an additive, perchloroethylene (PEC), flow of 3 ul/hr. The reaction pressure was about 400 psig. The hydrogenation product was analyzed by means of a gas chromatograph to determine the benzene content of the effluent. The tests were repeated by raising the temperature of the reaction and by changing the LHSV of the feedstock. These same tests were repeated without feed of the additive. The results are reported in Table I below.

TABLE I

| Run | LSHV | PCE | Temp. ° F. | Benzene Prod. ppm |
|-----|------|-----|------------|-------------------|
| A | 2 | yes | 100 | 10000 |
| B | 2 | yes | 120 | 400 |
| C | 2 | yes | 130 | 90 |
| D | 2 | yes | 160 | 3 |
| E | 4 | yes | 100 | 40000 |
| F | 4 | yes | 120 | 3000 |
| G | 4 | yes | 160 | 90 |
| H | 2 | No | 170 | 300 |
| I | 2 | No | 220 | 3000 |
| J | 2 | No | 230 | 30 |
| K | 4 | No | 175 | 2000 |
| L | 4 | No | 180 | 800 |

Table I above illustrates that the addition of the PCE provides the desired level of benzene hydrogenation, about 100 ppm, within the preferred range of temperature, 150° C.–250° C., in the presence of water in the ppm range. Without the PCE much higher temperatures were required, even though, as shown by run J, the desired level could be reached.

Reasonable variations, modifications and adaptations can be made within the scope of the disclosure and the appended claims without departing from the scope of this invention.

That which is claimed is:

1. In a process for the hydrogenation of benzene in a reaction zone containing an amount of water sufficient to deactivate the hydrogenation catalyst wherein the reaction zone contains (1) up to about 20% by weight benzene, (2) hydrogen gas, and (3) water in an amount up to about 30 parts per million parts by weight of a total feedstream that also contains the benzene and wherein the feedstream is contacted in the reaction zone with a hydrogenation catalyst comprising platinum under hydrogenation conditions including a temperature in the range of 100° F. to 300° F., the improvement comprising at least alleviating the deactivation of the catalyst caused by the presence of water by having at least one organic chlorine compound present in the reaction zone.

2. A process according to claim 1 wherein the organic chloride is chosen from the group consisting of monochloromethane, dichloromethane, trichloromethane, tetrachloromethane, monochloroethane, dichloroethanes, trichloroethanes, tetrachloroethanes, pentachloroethane, hexachloroethane, monochloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentanes, dichloropentanes, trichloropentanes, tetrachloropentanes, monochlorocyclopentane, chlorohexanes, dichlorocyclopentanes, trichlorocyclopentanes, monochloroethylene, 1,1-dichloroethylene, 1,2-dichloroethylene, trichloroethylene, tetrachloroethylene (perchloroethylene, PEC), chloropropylenes, chloro-n-butenes, chloroisobutenes, chloropentenes and mixtures of one or more thereof.

3. A process according to claim 2 wherein the organic chloride is tetrachloroethylene (perchloroethylene, PEC).

4. A process according to claim 1 in which the water is present in the reaction zone in an amount up to about 20 parts per million parts by weight of a total feedstream.

5. A process according to claim 1 wherein the amount of organic chlorine added to the feedstream is in the range of about 50–100 ppm of the total feedstream.

6. A process according to claim 4 wherein the conditions to hydrogenate in the reaction zone include a temperature in a range from about 150° F. to about 250° F.

* * * * *